United States Patent [19]

Casscells et al.

[11] Patent Number: 5,308,622
[45] Date of Patent: May 3, 1994

[54] TREATMENT OF VASCULAR INJURY

[75] Inventors: Ward M. Casscells, La Jolla; Douglas A. Lappi, Del Mar; J. Andrew Baird, San Diego, all of Calif.

[73] Assignee: The Salk Institute for Biological Studies, San Diego, Calif.

[21] Appl. No.: 915,056

[22] Filed: Jul. 16, 1992

Related U.S. Application Data

[63] Continuation-in-part of Ser. No. 637,074, Jan. 3, 1991, abandoned.

[51] Int. Cl.$^5$ ............................................. A61K 37/02
[52] U.S. Cl. ...................................... 424/422; 514/2; 514/21; 530/350; 530/399; 530/402
[58] Field of Search ............... 424/422; 530/399, 402, 530/350; 516/2, 21

[56] References Cited

U.S. PATENT DOCUMENTS 4,956,455  9/1990  Esch et al. .......................... 530/827
5,084,556  1/1992  Brown ................................. 424/85.1

FOREIGN PATENT DOCUMENTS 9012597  11/1990  PCT Int'l Appl.

OTHER PUBLICATIONS

Lappi et al BBRC 160 #2, p. 917, 1989.
Circulation, Supplement III, vol. 82, No. 4, Oct. 1990; Ward Casscells, et al., "Smooth Muscle Proliferation in Vessel Injury is Inhibited by a Toxin-Fibroblast Growth Factor Conjugate".
Circulation Research, vol. 68, No. 1, Jan. 1991; V. Lindner, et al.; "Role of Basic Fibroblast Growth Factor in Vascular Lesion Formation".

Primary Examiner—G. S. Kishore
Attorney, Agent, or Firm—Fitch, Even, Tabin & Flannery

[57] ABSTRACT

Patients suffering vascular injury as a result of balloon catheterization or the like are treated with medicaments containing conjugates comprising a ligand, such as bFGF (or another FGF polypeptide), and a cytotoxic agent. The cytotoxic agent can be a ribosome-inactivating protein (RIP), such as saporin, which is attached to the ligand through a chemical bond or prepared as a recombinant DNA chimera. The medicament containing the conjugate is administered IV to patients after they have been treated for atherosclerosis in a manner which commonly results in vascular injury, particularly to the intima, and effectively prevents restenosis. The conjugate kills proliferating smooth muscle cells in the lumen of the blood vessels which surprisingly express large numbers of high-affinity bFGF receptors while not inhibiting the growth of endothelial cells.

7 Claims, No Drawings

TREATMENT OF VASCULAR INJURY

This invention was made with Government support under Grant AM-18811 awarded by the National Institutes of Health (DHHS). The Government has certain rights in this invention.

This application is a continuation-in-part of application Ser. No. 07/637,074, filed Jan. 3, 1991, now abandoned.

This invention generally relates to the use of fibroblast growth factor ligands conjugated to cytotoxic agents in a manner to inhibit undesired cell proliferation, and more specifically, to the treatment of patients who have experienced vascular injury by administering a mitotoxin that includes a ligand such as FGF, and more specifically to prevent restenosis.

BACKGROUND OF THE INVENTION

Despite declining fatality rates, atherosclerosis remains the leading killer in industrialized nations. Many attempts have been made to prevent or to reverse atherosclerosis, and also to prevent rapid smooth muscle and other proliferation which may contribute importantly to pulmonary hypertension, transplant rejection, and restenosis after angioplasty or bypass grafting. Such attempts have included the use of antihypertensive and cholesterol-lowering agents, fish oils, corticosteroids, cyclosporin A, heparin and non-anticoagulant heparin fragments, inhibitors of angiotensin-converting enzyme, calcium antagonists, aspirin, prostacyclin and other modulators of platelet and smooth muscle eicosanoid metabolism, colchicine, terbinafine, triazolopyrimidine, analogues of somatostatin, anti-neoplastic agents, seeding with endothelial cells, and devices intended to produce less vascular trauma than balloon angioplasty, such as laser angioplasty and atherectomy. Although preliminary results in experimental animals and in humans show promise for some of these therapies, most will require sustained or local application.

Basic fibroblast growth factor (bFGF) is a protein which has a molecular weight of approximately 16 kD, is acid- and temperature-sensitive and has a high isoelectric point. A structurally related protein, acidic FGF (aFGF), has an acidic isoelectric point. FGFs exhibit a mitogenic effect on a wide variety of mesenchymal, endocrine and neural cells. Of particular interest is their stimulatory effect on collateral vascularization and angiogenesis. Such mitogenic effects have stimulated considerable interest in FGFs as potential therapeutic agents for wound healing, nerve regeneration and cartilage repair, for example.

New capillary growth takes place by a series of sequential steps beginning with the dissolution of the capillary basement membrane. Microvascular endothelial cells stimulated by angiogenic substances, such as BFGF, in vitro secrete collagenase, plasminogen activator, and stromelysin which degrade the basement membrane and allow endothelial cells to migrate toward the angiogenic stimulus. After migrating, the endothelial cells proliferate, develop sprouts, form capillary-like hollow tubules, and finally link tubules into capillary loops.

Many cells that respond to basic FGF have been shown to possess specific receptors on the cell surface membranes. The receptor proteins appear to be single chain polypeptides with molecular weights ranging from 110 to 150 kD, depending on cell type. These receptor proteins bind basic FGF with high affinity ($K_d = 10$–80 pill), and receptor numbers often range from 2000 to 80,000 per cell. Such receptors have been purified from chicken embryo and from rat brain, using a combination of lectin and ligand affinity chromatography and are associated with tyrosine kinase activity, see Imamura et al., *B.B.R.C.*, 583–590 (1989); Huang and Huang, *J. Biol. Chem.*, 261, 9568–9571 (1986).

On baby hamster kidney cells (BHK), two basic FGF receptors with estimated molecular weights of 110 and 130 kD have been reported in Neufeld et al., *J. Biol. Chem.*, 260, 13860–13868 (1985) and Neufeld et al., *J. Biol. Chem.*, 261, 5631–5637 (1986). Although both receptor proteins bind basic FGF and acidic FGF, it appears that the larger receptor protein binds bFGF preferentially and is sometimes referred to as the "high affinity" BFGF receptor; the smaller receptor has somewhat greater affinity for acidic FGF.

The feasibility of using receptor-specific ligands to transport toxins into cells has recently been demonstrated. The strategy, originally applied in immunotherapy by conjugating toxins to monoclonal antibodies (see Blakey et al., *Cancer Research*, 48, 7072–7078 (1988)), has recently been pursued by coupling toxins with classic endocrine hormones, such as CRF and TRF, with cytokines such as EGF and TGFα and with lymphokines such as interleukin-2. U.S. Pat. No. 4,468,382 to Bacha et al. shows cytotoxic conjugates wherein the hormone TRH is covalently linked to the toxin CRM 45 by bifunctional cross-linking agents to produce a toxic hybrid protein alleged to be useful in the treatment of certain tumors.

Atherosclerosis, sometimes referred to as arteriosclerosis, results from the development of an intimal lesion and the subsequent narrowing of the vessel lumen. Commonly, atherosclerosis originally appears as a result of the buildup of plaque which lines the interior of blood vessels, particularly the arteries. Whereas bypass surgery is sometimes employed to replace such clogged arteries, in recent years, a number of surgical procedures have been developed so as to interarterially remove such plaque, often by balloon catheterization or other such treatments in which the plaque is either compressed against or scraped away from the interior surface of the artery. Not infrequently, the patient so treated finds a recurrence of such narrowing of the vessel lumen in a relatively short period thereafter, generally referred to as restenosis, requiring a repetition of the surgical procedure to again remove the increasing blockage. A real need exists for preventing such recurrence in patients who have been treated for atherosclerosis.

SUMMARY OF THE INVENTION

Basic fibroblast growth factor (bFGF) has never been implicated in atherosclerosis or in neointimal hyperplasia in response to vascular injury; however, it has now been surprisingly found that the administration of a conjugate of a ligand, such as bFGF, and a cytotoxic agent can effectively prevent neointimal hyperplasia. Although bFGF mRNA, FGF receptor mRNA and bFGF protein are nearly undetectable in normal rat vessels, it has now been found that they are expressed after injury, particularly after dilation or crush injury, which can cause neointimal hyperplasia and can result in restenosis.

Coupling a ligand, such as basic FGF, to saporin-6 (SAP), a ribosome-inactivating protein (RIP) isolated from the seeds of the plant *Saponaria officinalis*, produces a powerful mitotoxin (FGF-SAP) i.e., a cytotoxic molecule targeted to specific cells by a mitogen. Certain conjugates like these are disclosed in International Application published Nov. 1, 1990 as WO 90/12597. It has been found that after treatment of arteries by balloon catheter or the like, denudation of the interior wall of the vessel occurs, with the endothelial cells which constitute the lining of the blood vessels being removed in multiple different locations. As a result of this removal, the smooth muscle cells (SMCs), which are normally located exterior of the endothelial cells (ECs) and form the blood vessel structure, begin to grow and multiply. As a consequence, there is a tendency for these smooth muscle cells to express functional high-affinity bFGF receptors and to proliferate so as to again fill the interior of the blood vessel, much in the same manner which it was previously clogged by the buildup of plaque, resulting in restenosis. In addition to counteracting restenosis, it is necessary that the endothelial cells grow so as to repair the lining of the blood vessel that was removed or damaged.

It has now been discovered that such undesirable growth of these proliferating, migrating smooth muscle cells in the interior of blood vessels, which can result in restenosis, can be inhibited by the administration of conjugates of appropriate ligands and cytotoxic agents, such as FGF-SAP. However, it has been surprisingly found that administration of this conjugate does not inhibit the growth of ECs necessary to create re-endothlialization and, in certain dosages, actually stimulates the growth of ECs while killing proliferating sacs.

Administration of a medicament containing conjugates of bFGF-saporin in a manner so as to reach the region where such cells expressing these receptors are proliferating has been found to result in the invasion of these cells and the inhibition of both protein and DNA synthesis, killing the cells; and this has been demonstrated with proliferating smooth muscle cells both in vitro and in vivo. Treatment is effected by administering a therapeutically effective amount of a medicament containing the conjugate in a physiologically acceptable carrier or recipient, in a manner so that the conjugate reaches regions in a human or other mammal where the cytotoxic agents then inhibit the proliferation of the target cells. Although a single dose inhibits neointimal proliferation, IV administration over a period of time is preferred.

DETAILED DESCRIPTION OF THE PREFERRED EMBODIMENTS

A key event in arteriosclerosis is the development of an intimal lesion with subsequent narrowing of the vessel lumen. Smooth muscle cell replication occurs after balloon catheter denudation of the rat carotid artery, and a comparison of two methods of experimental arterial injury has shown that smooth muscle replication appears to correlate with medial damage rather than with complete endothelial loss. This suggests the possibility that injury-induced release of endogenous mitogens, such as basic fibroblast growth factor (bFGF) may play a pivotal role in the subsequent responses of the vascular wall. bFGF is known to be synthesized by both endothelial and smooth muscle cells (SMCs) and is thought to be stored in the subendothelial matrix, and in some instances, this growth factor is released from cells after injury. Further investigation has now shown that bFGF is a potent mitogen for migrating SMCs of injured arteries, that continuous administration of bFGF could greatly increase arterial lesion size, and that administration of a conjugate of a ligand, such as bFGF, and a cytotoxic agent can prevent such undesirable intimal SMC growths in injured arteries in standard adult male Sprague-Dawley rats, without concurrently inhibiting desired EC growth.

Testing has now shown that basic FGF infused intraarterially into animals immediately after balloon catheter denudation or after denudation of endothelium by a less traumatic technique using a filament loop (which removes all the endothelium but does not significantly damage the underlying tunica media) causes a significant increase in smooth muscle cell proliferation.

Normally, 6 weeks after balloon injury, a substantial intimal thickening has formed, yet the smooth muscle replication is low. bFGF infused 6 weeks after denudation showed that replication of the intimal smooth muscle cells from the de-endothelialized segment of the carotid artery was significantly increased by the administration of bFGF, with the intimal cells in close proximity to the lumen showing the highest proliferation rate.

After first demonstrating that bFGF was mitogenic for both medial and intimal smooth muscle cells following injury, prolonged bFGF administration was carried out to evaluate its effect on intimal thickening formation. It was shown that the intimal area of bFGF-treated animals was significantly increased, i.e. it was approximately twice as large as the intima from control animals.

It has now been found that treatment with conjugates of a cytotoxic agent and a ligand, such as bFGF, or another FGF polypeptide reactive with an FGF receptor, will effectively inhibit growth and proliferation of certain cells which express functional high-affinity bFGF receptors without substantial undesirable side effects. By inhibiting proliferation of migrating smooth muscle cells (SMCs), it is possible to prevent the undesirable growth and ultimate clogging which occurs following vascular injury, and which is generally referred to as restenosis. The conjugates employed comprise a ligand, such as basic FGF or another FGF polypeptide (or equivalent non-peptide), which is reactive with the high-affinity FGF receptor and a cytotoxic agent, particularly a ribosome-inactivating protein (RIP), such as saporin—although other cytotoxic agents can also be advantageously used. The cytotoxic agent can be attached to the ligand through a chemical bond; alternatively, the composition can be prepared as a chimera, using recombinant DNA techniques. In either case, the conjugate molecule is designed and produced in such a way that the receptor-binding epitope of the ligand moiety of the complex is left available for recognition by the high-affinity FGF receptor. Surprisingly, it has been found that administration of the conjugate of bFGF and saporin does not inhibit the growth of ECs and at certain levels may stimulate the growth of ECs and thus promote the repair of blood vessel linings.

In addition to basic FGF (bFGF) and acidic FGF (aFGF), there are known to be a number of other proteins exhibiting basic FGF mitogenic activity mediated through binding to an FGF receptor. Moreover, it is now possible to design non-peptide equivalents of the polypeptide bFGF which will also bind to and activate the bFGF receptor. Mammalian basic FGF is a 146-residue peptide having a molecular weight of about 16 kD, and a pI of about 9.6, which may have an amino terminal extension. Other FGF proteins in addition to aFGF include *HST, INT/2*, FGF-5, FGF-6, and KGF(FGF-7), see Baird et al., *Brit. Med. Bull*, 45, 438–452 (1989). All induce mitogenic activity in a wide variety of normal diploid mesoderm-derived and neural crest-derived cells. A test of such "FGF mitogenic activity" is the ability to stimulate proliferation of cultured bovine aortic endothelial cells, as described in Gospodarowicz et al., *J. Biol. Chem.*, 257, 12266-12278 (1982) and Gospodarowicz et al., *P.N.A.S.*, 73, 4120–4124 (1976). The term FGF is broadly used herein to include proteins having amino acid sequences found in mammalian hosts, as well as modified sequences, i.e. having amino acid substitutions, deletions, insertions or additions, which still exhibit mitogenic activity mediated through binding to the high-affinity FGF receptor. For example, purified preparations of native bFGF and aFGF are frequently observed to include several molecular forms of the mitogens, such as shortened fragments; moreover, differences in amino acid sequences occur in FGFs from different species. The term FGF is thus intended to encompass proteins isolated from natural sources, polypeptides made synthetically, either by recombinant means or by chemical synthesis, as well as chemically designed equivalent non-peptides reactive with the high-affinity bFGF receptor.

The amino acid sequence of an exemplary mammalian bFGF obtained from bovine pituitary tissue is reported in Esch et al., *P.N.A.S.*, 82, 6507-6511 (1985); it is also set forth in U.S. Pat. No. 4,956,455, issued Sep. 11, 1990. The term "bFGF" should be generally understood to refer to proteins or polypeptides having substantially the same amino acid sequence and mitogenic activity as that of bovine bFGF or human bFGF. cDNAs encoding human aFGF, see Jaye et al., *Science,* 233, 541–545 (1986); bovine bFGF, see Abraham et al., *Science,* 233, 545–548 (1986), human bFGF, see Abraham et al., *EMBO J.*, 5, 2523–2528 (1986), and Abraham et al., *Quant. Biol.*, 51, 657–668 (1986), and rat bFGF, see Shimasaki et al., *B.B.R.C.* (1988) and Kurokawa et al., *Nucleic Acids Res.*, 16, 5201 (1988) have been cloned and sequenced; they predict the existence of proteins identical, or very highly homologous to bovine bFGF and aFGF found by protein sequencing.

As used herein, the term "FGF receptor" is used to refer to receptors, particularly the high-affinity receptors, which are able to bind basic FGF and transport it into the cell. Included among these are the receptors described in T. Imamura, *B.B.R.C.*, 155, 583–590 (1988) and in Moscatelli, *J. Cell. Physiol.*, 131, 123–130 (1987). As used herein, the term "ligand reactive with the FGF receptor" refers to any polypeptide or non-peptide equivalent which is capable of binding an FGF receptor and of being transported into the cell thereby.

Basic FGF is commercially available, for example, from Amgen (Thousand Oaks, Calif.) and from Amersham International. It can also be obtained from a variety of tissue types of mammals via methods of purification using reverse-phase high performance liquid chromatography (RP-HPLC) and/or heparin-Sepharose affinity chromatography. In addition, bFGF can be synthesized using recombinant methods. Expression of a recombinant protein in yeast and *E. coli* is described in Barr et al., *J. Biol. Chem.*, 263, 16471-16478 (1988) and in U.S. Pat. No. 4,956,455.

Such an FGF-cytotoxic agent conjugate can be purified on an affinity column containing immobilized heparin—for example, columns of heparin-Sepharose or heparin-agarose. The bound conjugate can be eluted with a salt gradient, such as NaCl, and elutes between 1 and 3M NaCl.

The ligand, e.g. bFGF, conjugated to a cytotoxic agent, is used to target the cytotoxic agent to specific cells of interest. As used herein, the term cytotoxic agent refers to a molecule capable of inhibiting cell function. The term includes agents which are only toxic when transported into the cell and also those whose toxic effect is mediated at the cell surface. A variety of cytotoxic agents can be used, particularly those which inhibit protein synthesis. As one example, bFGF is combined with a ribosome-inactivating protein (RIP) such as, for example, saporin-6 (SAP) or other SAP derivatives. SAP is a potent RIP which is isolated from the seeds of the plant *Saponaria officinalis,* see Stirpe et al., *Biochem J.*, 216, 617-625 (1983). other appropriate cytotoxic agents include, but are not limited to, ricin, ricin A chain, gelonin, diphtheria toxin, diphtheria toxin A chain, pokeweed antiviral protein (PAP), and Pseudomonas exotoxin. Alternatively, it may be feasible to use a drug as the cytotoxic agent; examples of such drugs include anthracyclines, such as the daunomycins (including daunorubicin and doxorubicin) and methotrexate and its analogs.

A ligand, such as bFGF, is suitably conjugated to a protein cytotoxic agent by known chemical reactions, such as through derivatization with a reactive sulfhydryl-containing moiety, such as SPDP, or via a cross-linking agent, such as glutaraldehyde or carbodimide. For example, the cytotoxic agent may be derivatized with a reactive sulfhydryl-containing agent, such as N-succinimidyl-3(2-pyridyldithio)propionate, before bFGF is added and mixed therewith. The bFGF conjugate can be separated from the unreacted products on a suitable column. Alternatively, bFGF can be conjugated to a drug, such as 14-bromo doxorubicin through the sugar moiety, as by the cis-aconitase method, see Shen and Riser, *B.B.R.C.*, 102, 1048 (1981).

Alternatively, it may be possible to prepare chimeric FGF-conjugates by recombinant methods. Such methods as applied to conjugates of IL-2 or TGFα are described in Chaudhary et al., *P.N.A.S.*, 84, 4538–4542 (1987) and in Lorberman-Galski et al., *P.N.A.S.*, 85, 1922-1926 (1988). See also Maniatis et al., *Molecular Cloning: A Laboratory Manual,* Cold Spring Harbor Laboratory (1982).

As hereinbefore indicated, it was unexpectedly found that vascular injury led to expression of very large numbers of high-affinity FGF receptors migrating SMCs. Indeed, within 24 hours of balloon dilation and de-endothelialization of the rat carotid artery, or injury of the lung by endotoxin, Northern analysis revealed expression of 4.2 and 2.7 kb transcripts that hybridized with a cDNA for the FGF receptor gene. In situ hybridization also revealed hybridization of an anti-sense cRNA for the FGF receptor gene. Moreover, autoradiograms of histologic sections revealed high affinity binding of bFGF (i.e., not displaceable by heparin infusion) to neo-intimal and medial migrating smooth muscle cells of injured vessels but not to quiescent smooth muscle cells of normal vessels; this binding was noted within 24 hours of injury. It was competed by excess bFGF; however, heat-denatured tracer was not bound. It is felt that the majority of such binding must have been to smooth muscle cells based on the light microscopic morphology and on the fact that leukocytes constitute a small minority of the medial cell population at this time.

The proliferating smooth muscle cells, as well as monocute/macrophages, also revealed immunocytochemical reactivity with peptide antisera raised against intra- and extra-cellular domains of the mouse FGF receptor clone. Injured vessels also revealed increased bFGF expression by specific immunocytochemistry using several monoclonal and polyclonal antibodies (which gave no stain after adsorption with excess ligand) and by in situ hybridization. Thus, injury, like culturing, induces expression of both bFGF and an FGF receptor.

Thymidine incorporation by medial smooth muscle cells began by 24 hours and was maximal at 48-96 hours. Areas of thrombosis and leukocyte attachment and infiltration were noted from 24-72 hours. Subsequently, cells migrated across damaged internal elastic laminae and proliferated in the neointima. DNA synthesis declined gradually but had not normalized by 14 days. A neointima was noted by 7 days and by 14 days it was 6-20 cells thick.

Although saporin itself is not believed to be toxic to most cells, if saporin is conjugated to bFGF, it is taken up by cells that express the high-affinity bFGF receptor and becomes a potent toxin that causes cell death. It was anticipated that this mitotoxin would compete for receptor binding of bFGF in SMCs and mediate cell death after internalization, resulting in widespread cell death after administration of this mitotoxin. Six weeks following denuding of endothelium with a balloon catheter from one artery of a group of rats, equimolar concentrations of bFGF conjugated to saporin (bFGF-SAP) or of unconjugated bFGF and saporin were infused intraarterially immediately prior to balloon injury. Loss of medial SMCs in the denuded arteries was observed.

It was found that bFGF conjugated to saporin, when infused in balloon catheter-denuded vessels caused a significant decrease in the number of migrating SMCs in such arteries, reflective of widespread cell death. Saporin not conjugated to bFGF was found not to be toxic to such SMCs because saporin by itself does not appear to be readily transported into such cells. When bound to bFGF, however, saporin is carried into these cells via the high-affinity bFGF receptor-mediated pathway leading to cell death. It is believed that, under normal circumstances, an intact endothelium may act as a permeability barrier to both bFGF and the bFGF-saporin conjugate preventing their contact with the underlying SMCs. Because re-endothelialization is also a requirement and because it is well known that ECs are stimulated by bFGF, the potential effect of the bFGF-SAP conjugate on ECs was of interest; it was surprisingly found that levels of bFGF-SAP which kill proliferating SMCs do not have an adverse effect upon ECs and some actually stimulated the growth of ECs.

To prove that such smooth muscle cell proliferation could be inhibited by bFGF-saporin, rabbit aortic SMCs from 8th passage were plated at 30,000 cels/cm$^2$ in 10% FBS in leucine-free M199. At 20 hours, cells received 0.01-10 nM bFGF-saporin conjugate. At 14, 18 or 24 hours, cells were pulsed for 2 hours with 1 $\mu$Ci/0.5 ml 3H-leucine, then chased with leucine-containing M199 for 2 hours and counted by liquid scintillation. This experiment was repeated once, with similar results, using rat aortic SMCs.

In 10% serum, 10 nM bFGF-saporin inhibited protein synthesis by 24 hours. Cell death began by 24-48 hours. Cells were killed by as little as 1 hour exposure to bFGF-saporin followed by a heparin wash to remove bFGF-saporin from heparin sulfates on the cell surface. Saporin alone inhibited cell growth only at substantially higher concentrations of 0.1-1.0 $\mu$M. By 96 hours after a single exposure to 10 nM bFGF-saporin, only 10% of cells were viable as indicated by exclusion of trypan blue. Rat ECs isolated from the supernatant of collagenase-digested aortas were plated and grown under similar circumstances in DMEM with high glucose. It was found that, over a fairly wide range of concentrations, e.g. from about 0.1 to about 1 nanomolar bFGF-SAP, wherein there was inhibition of growth of SMCs, growth of ECs was stimulated.

Even quiescent cells require protein synthesis, and the survival of such cells may be due to resistance to saporin in some or to a failure of bFGF-SAP to enter the cells. SMCs appear to have few or no FGF receptors when quiescent, but after balloon injury of the carotid artery, local application of bFGF-SAP kills proliferating SMCs and intravenous administration of bFGF-SAP inhibits their migration and proliferation.

In standard adult male Sprague-Dawley rats subjected 24 hours earlier to balloon injury of the carotid artery, the administration of 1 or 10 $\mu$g bFGF-saporin (instilled into a temporary pouch made by occluding the artery proximally and distally for 15 minutes) resulted in the death of most medial smooth muscle cells, and 75% fewer neointimal cells (compared to controls) were detected 14 days after injury. In the arteries of treated rats, there was as much thrombus as in saline controls, and even more inflammation. Since macrophages express multiple growth factors, and thrombin and fibrin are mitogenic for smooth muscle cells, the abundance of these processes suggests that bFGF-saporin is not acting indirectly, e.g., by a (hypothetical) anti-inflammatory or anti-thrombotic action. It appears that bFGF-saporin directly killed migrating smooth muscle cells and that this injury accentuated the thrombotic and inflammatory responses to the balloon injury.

Rats given intravenous bFGF-saporin as a single 25 $\mu$g dose 24 hours after balloon injury developed 24% less neointimal proliferation at 14 days as measured by surface area. For these standard adult Sprague-Dawley rats, which have an average weight of about 325 grams, this dose translates to about 75 micrograms per kilogram of body weight. In this model, there was almost no evidence of thrombosis at 14 days, and inflammation was much less marked than in the rats treated by local infusion. In fact, the absence of necrosis in the rats treated with bFGF-saporin suggests that some of the effect is due to an inhibition of proliferation and/or migration rather than cell killing.

In the in vitro testing of SMCs and ECs in culture, it was found that, over a fairly wide range of concentrations, bFGF-SAP inhibited the growth of SMCs yet stimulated, the growth of ECs. To test the effect of bFGF-SAP on ECs in vivo, rat aortas were de-endothelialized by being subjected to balloon catheter injury as described hereinbefore. A group of young male rats, about 250 g. average weight, were given an IV injection of about 12.5 $\mu$g of bFGF-SAP per day (equal to a dosage of about 50 $\mu$g/kg daily) while other groups of rats were treated with phosphate-buffered saline (PBS) or with saporin in PBS. After four days, the anterial system surfaces were stained with Evans blue dye, and the rats thereafter sacrificed. The regions that have been re-endotheliaized are impermeable to the dye and thus remain unstained. Examination of the pertinent regions shows that there is no significant difference in the re-endotheliaized areas among the three groups of rats tested, showing that there was no inhibition of the growth of ECs by the conjugate. The experiment is to be repeated with relatively aged rats and also with rats that are inflicted with diseases that create a more slowly growing endothelium than the younger rats tested, and based upon the in vitro test results, it is expected that, in such rat models, the administration of the bFGF-SAP conjugate at a level of about 0.1 mg/kg will result in actual stimulation of such relatively slowly growing ECs.

The effect of bFGF-SAP upon pulmonary vascular injury, thrombosis, inflammation and smooth muscle proliferation caused by endotoxin was also investigated. Endotoxin causes death of some endothelial cells while others are stimulated to produce leukocyte adhesion molecules, pro-coagulant factors and cytokines mitogenic for smooth muscle cells, such as interleukin 1, PBGF-B chain, TNF and endothelin. Rats were given 1 $\mu$g lipopolysaccharide intraperitoneally ($2 \times 10^4$ endotoxin units/$\mu$g, Ribi Immunochem, Hamilton, Mont.), followed by 24 hours by 10 $\mu$g saporin or bFGF-saporin, IV. Following sacrifice on day 7, there were fewer foci of injury in those treated with the conjugate, and many vessels in fact appeared thinned. Intravascular thrombi in rats treated with saporin contained smooth muscle cells, while those in rats treated with bFGF-saporin had none.

Present therapies for the treatment of atherosclerosis, for example balloon catheterization, inherently result in some injury to the endothelial lining of blood vessel walls, thereafter requiring follow-on local application. Although it can be administered locally, a medicament containing a bFGF-saporin conjugate is in theory self-targeting after intravenous injection and is effective to prevent restenosis following such surgical treatment or the like. Moreover, one (or a few) doses should prove sufficient, thus avoiding such potential problems as allergic reactions or production of neutralizing antibodies. The bFGF-saporin conjugate also has the useful feature of binding to heparin-like species on the cell surface, and if bFGF receptors are expressed later in some cells than in others, the conjugate often remains in the region so as to be accessible once the receptor is expressed. The same advantage pertains if expression of the bFGF receptor is localized to only a portion of the cell cycle. A single treatment delivers the conjugate for temporary local storage, and because some cells internalize a small amount of heparin, FGF-SAP might be internalized even by cells not expressing FGF receptors. No obvious systemic toxicity is observed in normal animals receiving bFGF-saporin, and it may be that bFGF-SAP is cleared by binding of bFGF to alpha-2 macroglobulin, or shedding or degradation of cell surface heparin. Clearance might be accelerated by chasing with intravenous heparin, or with glutathione for reduction of bFGF-SAP disulfide bond.

Although local delivery of high concentrations of bFGF-SAP may be employed, the possibility of thrombosis indicates that intravenous administration, which did not produce necrosis or other obvious toxicity, is preferred. Because it appears that there are few FGF functional receptors in normal adult blood vessels, the toxicity of the bFGF-saporin conjugate should not have substantial undesirable side effects as a result of IV administration. Because replicating endothelial cells express FGF receptors, it was originally thought that reendothelialization of vascular wounds might be delayed by bFGF-SAP administration; moreover, wound-healing, in general, may be delayed if fibroblasts and activated leukocytes should express FGF receptors, or if their high levels of nonspecific phagocytosis cause them to ingest saporin. It was once felt that, after angioplasty, the delay for a few weeks of IV administration of bFGF-SAP (to allow healing of the femoral artery access puncture) might be preferred, because it would be effective to combat restenosis which is believed to develop over several months; however, this is no longer considered necessary, particularly because certain dosages can actually stimulate the growth of ECs.

For treatment of vascular injury, a therapeutically effective amount of a medicament containing an FGF-cytotoxic agent conjugate in a physiologically acceptable excipient is administered to a mammal. Examples of physiologically acceptable excipients include PBS (phosphate-buffered saline) and saline.

Preferably, the medicament containing the conjugate is administered intravenously (IV), although treatment by localized administration of the conjugate may be tolerated in some instances. Generally, the medicament containing the conjugate is injected into the circulatory system of a patient in order to deliver a dose of cytotoxin to the targeted cells by first binding the conjugate to high affinity bFGF receptors expressed by such cells.

The efficiency with which a cytotoxin, such as saporin or a Ricin A chain or a similar RIP, can inhibit protein synthesis and consequently interfere with DNA synthesis is fairly widely known. Accordingly, the dosage of the conjugate that is administered will, to some extent, depend upon the particular cytotoxin chosen; however, doses of the conjugate in the general range of about 0.01 mg to about 100 mg of the conjugate per kilogram of body weight are expected to be employed as a daily dosage. However, as indicated hereinbefore, there may be particular advantages in administering a daily dosage of about 0.1 mg/kg (i.e. between 0.05 and 0.3 mg/kg) which has the unique feature of preventing restenosis while stimulating growth of ECs to promote reendothelialization.

Although the invention has been described with reference to the presently-preferred embodiments, it should be understood that various changes and modifications can be made without departing from the spirit of the invention, which is defined by the claims appended hereto. Particular features of the invention are emphasized in the claims which follow.

We claim:

1. A method of preventing restenosis caused by smooth muscle cell proliferation in response to injury to the endothelial lining of blood vessel walls, which method comprises administering intravenously or locally an effective amount of a bFGF-saporin conjugate sufficient to prevent smooth muscle cell proliferation in the lumen of the blood vessel, while not inhibiting the regrowth of said endothelial lining.

2. The method of claim 1 wherein said amount administered is between approximately 0.01 mg and 100 mg of conjugate per kilogram of body weight per day.

3. The method of claim 1 wherein said amount administered is approximately 0.1 mg of conjugate per kilogram of body weight per day.

4. The method of claim 3 wherein said conjugate is administered intravenously.

5. The method of claim 4 wherein said conjugate is administered between 24 hours and six weeks after said injury.

6. The method of claim 2 wherein said conjugate is administered locally.

7. A method of preventing restenosis caused by smooth muscle cell proliferation in response to endotoxin damage to the endothelial lining or to damage from vascular surgery by balloon catheterization treatment, which method comprises intravenously administering an effective amount of FGF conjugated to a cytotoxic ribosome-inactivating protein, said amount of FGF-conjugate being sufficient to prevent smooth muscle cell proliferation in the lumen of the blood vessels while not inhibiting regrowth of the endothelial lining, said administering occurring between 24 hours and six weeks after damage.

* * * * *